US009579011B2

United States Patent
Ogasawara et al.

(10) Patent No.: US 9,579,011 B2
(45) Date of Patent: Feb. 28, 2017

(54) ENDOSCOPE SYSTEM THAT CONTROLS LASER OUTPUT OF LASER PROBE AND CONTROL METHOD FOR ENDOSCOPE SYSTEM

(71) Applicant: OLYMPUS CORPORATION, Tokyo (JP)

(72) Inventors: Kotaro Ogasawara, Tokyo (JP); Hitoshi Komine, Hachioji (JP); Nanako Ubayama, Hachioji (JP); Kentaro Hase, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/733,303

(22) Filed: Jun. 8, 2015

(65) Prior Publication Data

US 2015/0265134 A1 Sep. 24, 2015

Related U.S. Application Data

(63) Continuation of application No. PCT/JP2014/061837, filed on Apr. 28, 2014.

(30) Foreign Application Priority Data

Jun. 18, 2013 (JP) .................... 2013-127668

(51) Int. Cl.
*A61B 1/04* (2006.01)
*A61B 1/018* (2006.01)
(Continued)

(52) U.S. Cl.
CPC ...... *A61B 1/00006* (2013.01); *A61B 1/00009* (2013.01); *A61B 1/00087* (2013.01);
(Continued)

(58) Field of Classification Search
CPC ............ A61B 1/00006; A61B 1/00009; A61B 1/00087; A61B 1/018; A61B 2017/00296;
(Continued)

(56) References Cited

U.S. PATENT DOCUMENTS 5,893,828 A * 4/1999 Uram ..................... A61B 18/22
600/108
7,869,016 B2 * 1/2011 Mitchell ................ A61B 18/22
219/121.62

(Continued)

FOREIGN PATENT DOCUMENTS

EP 2 123 215 A1 11/2009
EP 2532299 A1 12/2012
(Continued)

OTHER PUBLICATIONS

International Search Report dated Aug. 5, 2014 issued in PCT/JP2014/061837.
(Continued)

*Primary Examiner* — John P Leubecker
(74) *Attorney, Agent, or Firm* — Scully, Scott, Murphy & Presser, P.C.

(57) ABSTRACT

An endoscope system includes: an endoscope including an insertion portion, an image pickup portion that acquires a plurality of images by time-sequentially picking up optical images of a subject by means of an objective optical system provided in a distal end portion of the insertion portion, and a channel that opens at the distal end portion of the insertion portion; a laser probe that is inserted through the channel; an image analysis portion that detects an area showing the laser probe with respect to each image; and a control portion that permits laser output only in a case where it is determined that the laser probe protrudes from the opening of the channel based on detection results with respect to the area
(Continued)

showing the laser probe for a plurality of images that are time-sequentially consecutive.

8 Claims, 9 Drawing Sheets

(51) Int. Cl.
*A61B 1/00* (2006.01)
*A61B 1/05* (2006.01)
*A61B 18/24* (2006.01)

(52) U.S. Cl.
CPC .............. *A61B 1/018* (2013.01); *A61B 1/05* (2013.01); *A61B 18/24* (2013.01); *A61B 2034/2065* (2016.02); *G06T 2207/10068* (2013.01)

(58) Field of Classification Search
CPC ............ A61B 2017/0034; A61B 18/24; A61B 2034/2065; A61B 2090/0811; G02T 2207/10068
USPC .......................................................... 600/108
See application file for complete search history.

(56) References Cited

U.S. PATENT DOCUMENTS

| | | | | |
|---|---|---|---|---|
| 8,497,898 | B2 | 7/2013 | Moriyama et al. | |
| 2002/0188285 | A1* | 12/2002 | Brown | A61B 1/0051 606/15 |
| 2004/0034277 | A1* | 2/2004 | Farkas | A61B 1/063 600/108 |
| 2009/0177191 | A1* | 7/2009 | Brown | A61B 18/24 606/12 |
| 2009/0198104 | A1* | 8/2009 | Sugiyama | A61B 1/00039 600/146 |
| 2010/0152538 | A1 | 6/2010 | Gleason et al. | |
| 2011/0208000 | A1* | 8/2011 | Honda | A61B 1/00016 600/118 |
| 2012/0182409 | A1* | 7/2012 | Moriyama | A61B 1/00006 348/65 |
| 2012/0271102 | A1 | 10/2012 | Katayama | |
| 2012/0287238 | A1* | 11/2012 | Onishi | A61B 1/0005 348/45 |
| 2013/0002844 | A1* | 1/2013 | Shida | A61B 1/00009 348/65 |
| 2013/0072753 | A1* | 3/2013 | Zappia | A61B 1/0008 600/108 |
| 2014/0243849 | A1* | 8/2014 | Saglam | A61B 19/2203 606/130 |
| 2015/0133728 | A1* | 5/2015 | Finkman | A61B 17/2202 600/108 |

FOREIGN PATENT DOCUMENTS

| | | |
|---|---|---|
| EP | 2612587 A1 | 7/2013 |
| JP | H04-325139 A | 11/1992 |
| JP | H08-280709 A | 10/1996 |
| JP | H09-094227 A | 4/1997 |
| JP | 2002-125926 A | 5/2002 |
| JP | 2002-238844 A | 8/2002 |
| JP | 2006-271871 A | 10/2006 |
| JP | 2008-212349 A | 9/2008 |
| WO | WO 2012/035923 A1 | 3/2012 |
| WO | WO 2013/005547 A1 | 1/2013 |

OTHER PUBLICATIONS

Extended Supplementary European Search Report dated Jun. 9, 2016 in related European Application No. 14 81 3411.7.

* cited by examiner

FIG. 3

| FRAME NUMBER | ... | n−1 | n | n+1 | n+2 | n+3 | n+4 | ... |
|---|---|---|---|---|---|---|---|---|
| ACQUIRED IMAGE | ... | | | 5i | 5i | 5i | 5i | ... |
| PROBE DETECTION RESULT | ... | NONE | NONE | NONE | YES | YES | YES | ... |
| LOGICAL VALUE | ... | FALSE | FALSE | FALSE | TRUE | TRUE | TRUE | ... |
| LOGICAL PRODUCT VALUE | ... | FALSE | FALSE | FALSE | FALSE | TRUE | TRUE | ... |
| LASER OUTPUT | ... | PROHIBITED | PROHIBITED | PROHIBITED | PROHIBITED | PERMITTED | PERMITTED | ... |

FIG. 5

| FRAME NUMBER | ... | n-2 | n-1 | n | n+1 | n+2 | n+3 | n+4 | ... |
|---|---|---|---|---|---|---|---|---|---|
| ACQUIRED IMAGE | ... | | | | 5i | 5i | 5i | 5i | ... |
| PROBE SIZE | ... | 0 | 0 | 0 | 1 | 2 | 3 | 4 | ... |
| AVERAGE VALUE | ... | 0 | 0 | 0 | 0.3 | 1 | 2 | 3 | ... |
| LASER OUTPUT | ... | PROHIBITED | PROHIBITED | PROHIBITED | PROHIBITED | PROHIBITED | PERMITTED | PERMITTED | ... |

FIG. 7

| FRAME NUMBER | ... | n−2 | n−1 | n | n+1 | n+2 | n+3 | n+4 | n+5 | ... |
|---|---|---|---|---|---|---|---|---|---|---|
| ACQUIRED IMAGE | ... | | | | | | | | | ... |
| PROBE SIZE | ... | 4 | 4 | 4 | 3 | 2 | 1 | 0 | 0 | ... |
| AVERAGE VALUE | ... | 4 | 4 | 4 | 3.7 | 3 | 2 | 1 | 0.3 | ... |
| LASER OUTPUT | ... | PERMITTED | PERMITTED | PERMITTED | PERMITTED | PERMITTED | PERMITTED | PERMITTED | PROHIBITED | ... |

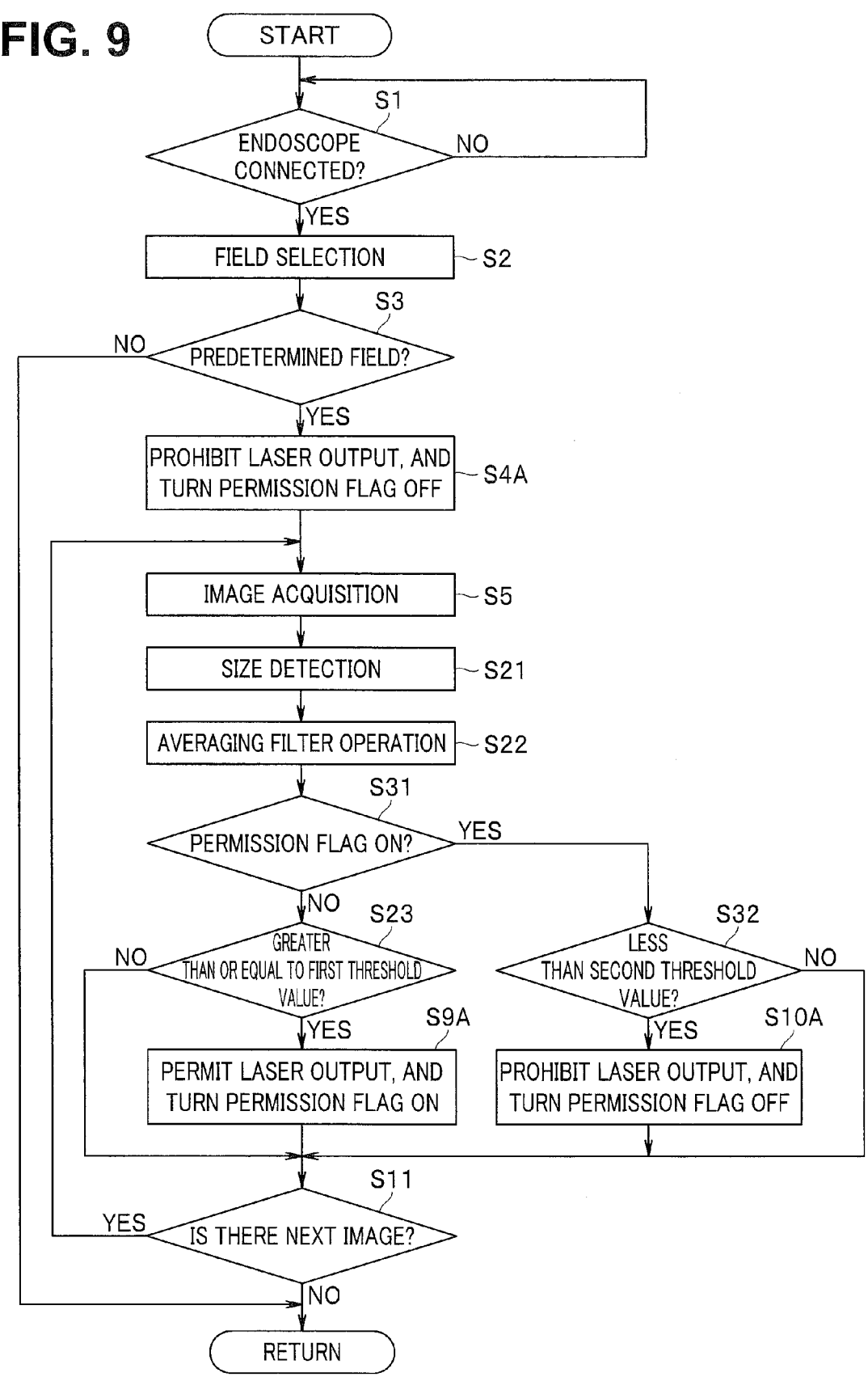

ENDOSCOPE SYSTEM THAT CONTROLS LASER OUTPUT OF LASER PROBE AND CONTROL METHOD FOR ENDOSCOPE SYSTEM

CROSS REFERENCE TO RELATED APPLICATION

This application is a continuation application of PCT/JP2014/061837 filed on Apr. 28, 2014 and claims benefit of Japanese Application No. 2013-127668 filed in Japan on Jun. 18, 2013, the entire contents of which are incorporated herein by this reference.

BACKGROUND OF THE INVENTION

1. Field of the Invention

The present invention relates to an endoscope system equipped with an endoscope and a laser probe that is inserted through an endoscope channel, and also to a control method for an endoscope system.

2. Description of the Related Art

Medical treatment is sometimes performed by inserting a treatment instrument through a channel provided in an endoscope, and causing a distal end of the treatment instrument to protrude from a distal end of the endoscope.

Since the aforementioned kind of treatment instrument is generally used in a state in which the distal end thereof has been caused to protrude from the distal end of an endoscope, it is desirable to check the protruding state thereof. Consequently, technology of various kinds has been proposed for detecting that a treatment instrument is protruding from the distal end of an endoscope.

For example, in Japanese Patent Application Laid-Open Publication No. 2002-125926, technology is disclosed in which the protrusion of a treatment instrument from the distal end of an endoscope is detected by a sensor such as a photo-interrupter. According to the technology described in the aforementioned publication, the detection result is used for controlling the magnification of an image.

Further, in Japanese Patent Application Laid-Open Publication No. 2008-212349, technology is disclosed that includes a forceps roller that is arranged in a proximal end portion of a forceps channel, a forceps encoder for detecting a rotation angle of the forceps roller, and a forceps detecting apparatus that detects the protrusion or retraction of a forceps from or into a distal end portion of the forceps channel based on rotation angle data from the forceps encoder. Further, according to the technology disclosed in the aforementioned publication, a detection result is used, for example, for an animated display of the protruding state of the forceps. In addition, in the aforementioned publication, technology is disclosed that, in a case where a detection result is that the forceps is not protruding, transitions to a stop mode to prohibit the passage of a high-frequency current to the treatment instrument.

In addition, in Japanese Patent Application Laid-Open Publication No. 2006-271871 technology is described that determines that a treatment instrument is positioned in the vicinity of a target site in a case where a signal of a predetermined luminance value or more is detected in a predetermined region within an observation field of view. According to the technology described in the aforementioned publication, a determination result is used as a trigger for starting video recording.

In this connection, in some treatment instruments a treatment portion for treating a subject by imparting energy to the subject is provided at the distal end of the treatment instrument. Examples of such treatment instruments include a laser probe that is described in the aforementioned Japanese Patent Application Laid-Open Publication No. 2002-125926, or a high-frequency treatment instrument that is described in the aforementioned Japanese Patent Application Laid-Open Publication No. 2002-125926 or Japanese Patent Application Laid-Open Publication No. 2008-212349. Surgery that pulverizes a stone by means of a laser beam in transurethral ureterolithotripsy may be mentioned as an example of treatment in which the laser probe of the former is utilized.

SUMMARY OF THE INVENTION

An endoscope system according to a certain aspect of the present invention includes: an endoscope having an insertion portion that is to be inserted into a subject, an objective optical system provided in a distal end portion of the insertion portion, an image pickup portion that time-sequentially picks up optical images of the subject that are formed by the objective optical system to acquire a plurality of images, and a channel that is provided inside the insertion portion so as to have a channel opening in the distal end portion of the insertion portion; a laser probe that is inserted through the channel of the endoscope and that outputs a laser beam from a distal end portion towards the subject; an image analysis portion that detects an area of the laser probe with respect to each of a plurality of the images that are time-sequentially acquired; and a control portion that determines whether or not the laser probe protrudes from the channel opening based on detection results with respect to the area of the laser probe which are obtained by the image analysis portion for a plurality of the images that are time-sequentially consecutive, and permits the laser probe to output the laser beam only in a case where it is determined that the laser probe protrudes.

Further, a control method for an endoscope system according to a certain aspect of the present invention is a control method for an endoscope system including: an endoscope having an insertion portion that is to be inserted into a subject, an objective optical system provided in a distal end portion of the insertion portion, an image pickup portion that time-sequentially picks up optical images of the subject that are formed by the objective optical system to acquire a plurality of images, and a channel that is provided inside the insertion portion so as to have a channel opening in the distal end portion of the insertion portion, and a laser probe that is inserted through the channel of the endoscope and that outputs a laser beam from a distal end portion towards the subject; the control method comprising: an image analysis step of detecting an area of the laser probe with respect to each of a plurality of the images that are time-sequentially acquired; and a control step of determining whether or not the laser probe protrudes from the channel opening based on detection results with respect to the area of the laser probe which are obtained in the image analysis step for a plurality of the images that are time-sequentially consecutive, and permitting the laser probe to output the laser beam only in a case where it is determined that the laser probe protrudes.

BRIEF DESCRIPTION OF THE DRAWINGS

FIG. 3 is a chart illustrating an example in which permission/prohibition of laser output is set based on a plurality of images that are time-sequentially acquired according to the aforementioned Embodiment 1;

FIG. 5 is a chart illustrating an example in which permission/prohibition of laser output is set based on a plurality of images that are time-sequentially acquired according to Embodiment 2 of the present invention;

FIG. 7 is a chart illustrating an example in which permission/prohibition of laser output is set based on a plurality of images that are time-sequentially acquired according to Embodiment 3 of the present invention;

FIG. 9 is a flowchart illustrating operations of the endoscope system in the aforementioned Embodiment 3.

DETAILED DESCRIPTION OF THE PREFERRED EMBODIMENTS

Embodiments of the present invention will be described hereunder with reference to the drawings.
[Embodiment 1]

Figure 1:
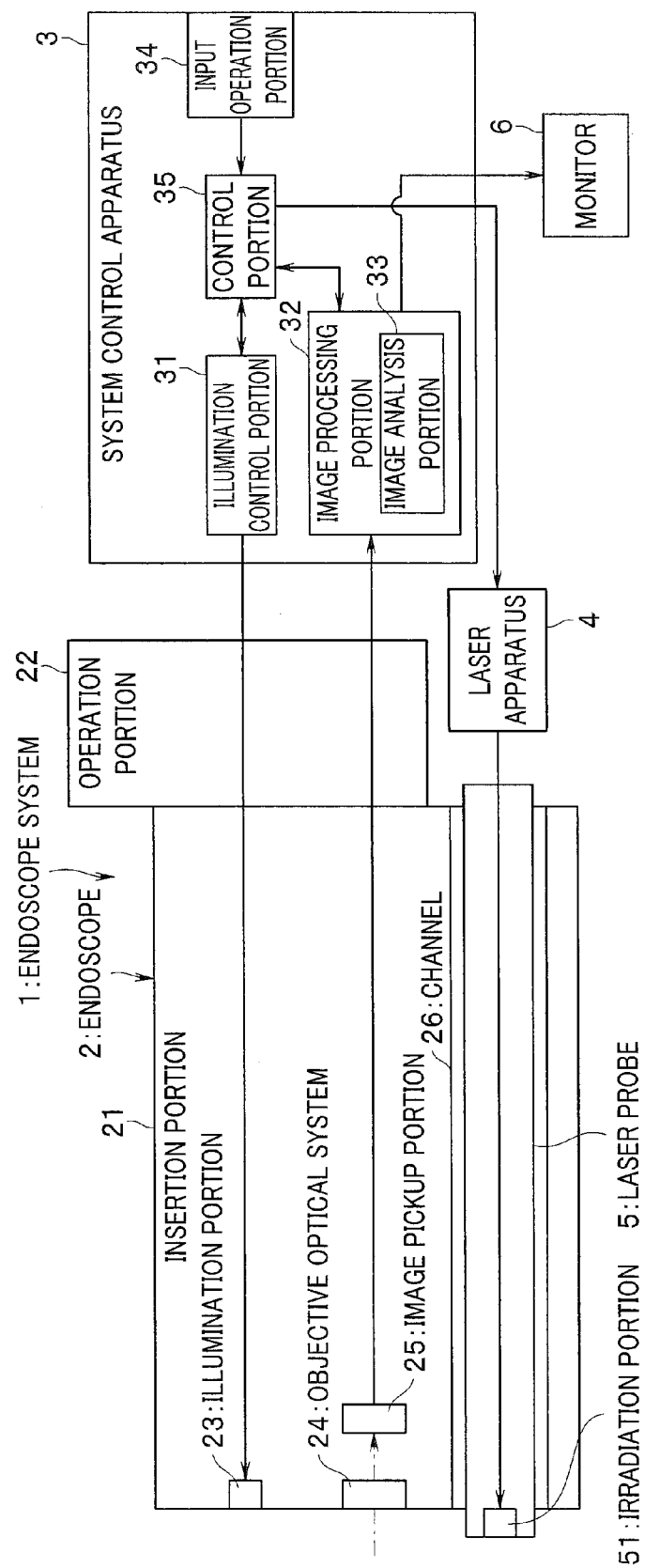
FIG. 1 is a block diagram illustrating the configuration of an endoscope system according to Embodiment 1 of the present invention.

FIG. 1 to FIG. 4 illustrate Embodiment 1 of the present invention. FIG. 1 is a block diagram showing the configuration of an endoscope system.

An endoscope system 1 includes an endoscope 2, a system control apparatus 3, a laser apparatus 4, a laser probe 5 and a monitor 6.

The endoscope 2 includes an elongated insertion portion 21 that extends from an operation portion 22 on the hand side towards a distal end side and that is for inserting into a subject.

An illumination portion 23, an objective optical system 24 and an image pickup portion 25 are arranged in a distal end portion of the insertion portion 21.

The illumination portion 23 emits an illuminating light towards a subject.

The objective optical system 24 forms an optical image of an illuminated subject.

The image pickup portion 25 time-sequentially picks up optical images of the subject that are formed by the objective optical system 24 to thereby acquire a plurality of images and, for example, includes an image pickup device in which a plurality of pixels are arrayed. Hereunder, a single image that is time-sequentially picked up and acquired is referred to as a "frame image" or the like.

Further, in the insertion portion 21, a channel 26 for inserting a treatment instrument from the hand side to the distal end side is provided so as to have a channel opening (hereunder, referred to as "distal end opening") in the distal end portion of the insertion portion 21.

The above described endoscope 2 is configured so as to be connected to and controlled by the system control apparatus 3.

The system control apparatus 3 includes an illumination control portion 31, an image processing portion 32 including an image analysis portion 33, an input operation portion 34 and a control portion 35.

The illumination control portion 31 controls the emission/non-emission of an illuminating light from the illumination portion 23 and the amount of illuminating light at a time of emission and the like.

The image processing portion 32 subjects an image that is outputted from the image pickup portion 25 to image processing such as color balance adjustment, gamma conversion, color conversion and conversion to a signal format for displaying on the monitor 6, and outputs the resulting image signal to the monitor 6.

The image analysis portion 33 included in the image processing portion 32 performs image analysis on each of a plurality of images that are time-sequentially acquired, and detects an image portion 5i (see FIG. 3) showing the laser probe 5 in the images. More specifically, although detection of the image portion 5i showing the laser probe 5 in an image that is performed by the image analysis portion 33 is performed, for example, based on a difference between a hue of the subject and a hue of the laser probe 5, a difference between a luminance of the subject and a luminance of the laser probe 5, a comparison between the shape of an edge that is obtained by applying an edge detection filter to the image and the shape of the contour of the laser probe 5 or the like, the detection of the image portion 5i showing the laser probe 5 in an image is not limited to the foregoing and it is also possible to detect the image portion 5i showing the laser probe 5 using other appropriate technology. However, hereunder an example is described in which the laser probe 5 is configured so as to have a surface that has a different hue to the hue of the subject, and the image analysis portion 33 detects the image portion 5i showing the laser probe 5 in an image based on a difference between the hue of the subject and the hue of the laser probe 5. The image processing portion 32 also performs an analysis of the number of pixels (area) of the image portion 5i showing the laser probe 5 or the like in conjunction with the aforementioned analysis.

The input operation portion 34 is a component for performing an operation input with respect to the system control apparatus 3, and is configured so as to enable operations to be performed to switch the power on and off and to perform settings for medical treatment field selection and the like. In this case, although the present embodiment is described on the basis that lap choly (laparoscopic cholecystectomy), urinary organs, otolaryngology and the like are medical treatment fields in which the endoscope system 1 is used (see FIG. 2), the endoscope system 1 may also be used in other medical treatment fields. Note that, in a broader sense, the endoscope system 1 is not limited to medical treatment fields and may be used in any field in which the endoscope system 1 can be used.

The control portion 35 controls the illumination control portion 31 to cause the illumination portion 23 to emit an illuminating light. The control portion 35 also controls so as to cause the image analysis portion 33 to analyze a plurality of images that are acquired time-sequentially. Further, only in a case where the image portion 5i showing the laser probe 5 is detected in accordance with a predetermined condition by the image analysis portion 33, the control portion 35 determines that the laser probe 5 is protruding from the distal end opening of the channel 26 and permits the laser probe 5 to output a laser beam. More specifically, the control portion 35 performs a logical product operation that takes a case where the image portion 5i showing the laser probe 5 is detected as "true" and takes a case where the image portion 5i showing the laser probe 5 is not detected as "false" with respect to a plurality of images (in the present embodiment, as one example, two images are assumed, although naturally the number of images is not limited to two) that are time-sequentially consecutive, and only permits the laser probe 5 to output a laser beam in a case where the result of the operation is "true". Accordingly, if the control portion 35 determines that the laser probe 5 is not protruding from the distal end opening of the channel 26, the control portion 35 prohibits laser output by the laser probe 5.

The laser probe 5 is configured to be inserted through the channel 26 of the endoscope 2, and includes, in a distal end portion thereof, an irradiation portion 51 for outputting a laser beam towards a subject.

The laser apparatus 4 controls the laser output from the irradiation portion 51.

The monitor 6 is a display apparatus that is connected to the system control apparatus 3 and that displays endoscopic images that were processed by the image processing portion 32 and various kinds of information relating to the endoscope system 1.

Figure 4:
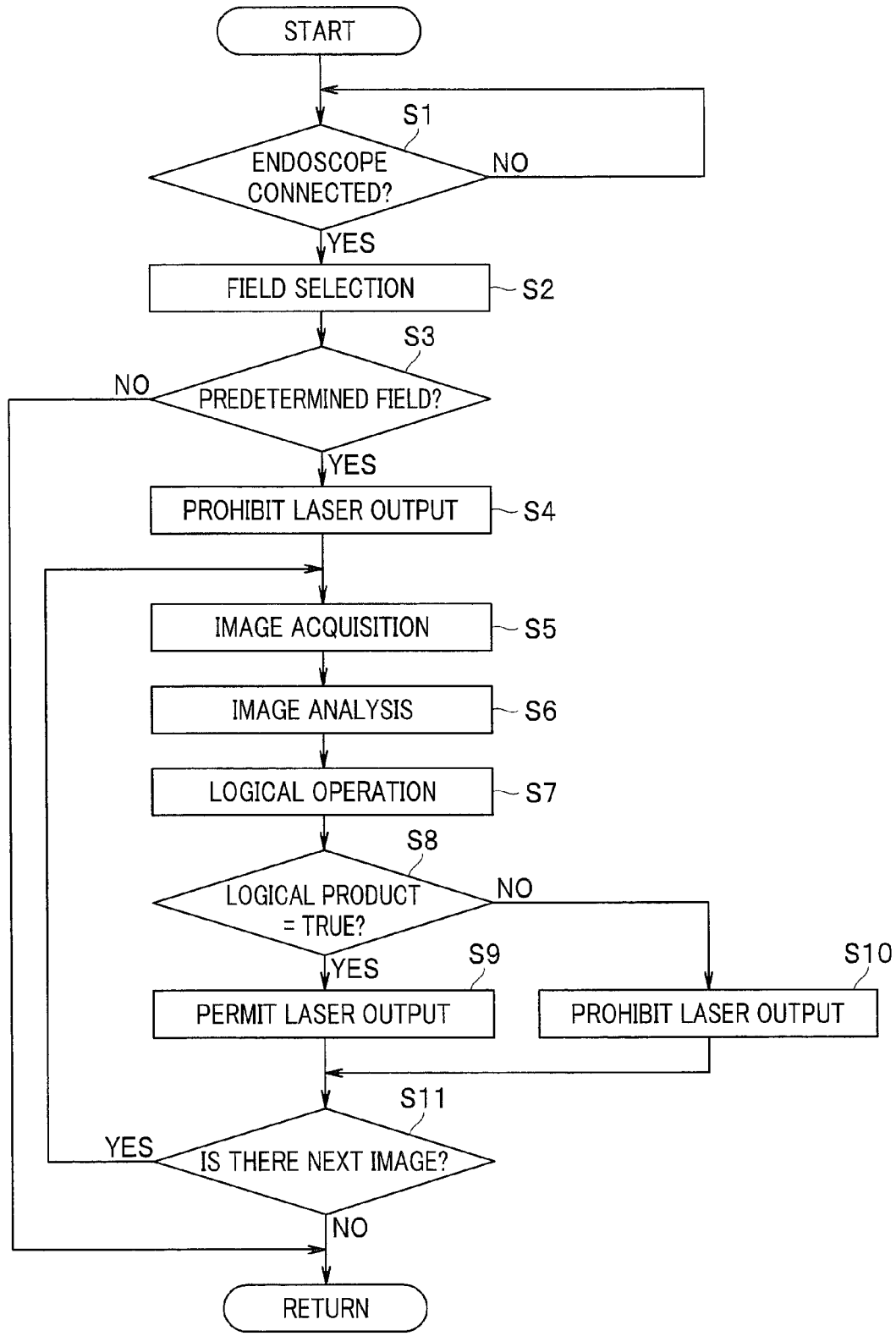
FIG. 4 is a flowchart illustrating operations of the endoscope system according to the aforementioned Embodiment 1.

The operations of the endoscope system 1 (and by extension, a control method for the endoscope system) will now be described in accordance with FIG. 4 while referring as appropriate to FIG. 2 and FIG. 3. FIG. 4 is a flowchart illustrating the operations of the endoscope system.

The processing shown in FIG. 4 is, for example, called from a main control processing routine for controlling the system control apparatus 3 (or the overall endoscope system 1) and executed.

Upon the start of the processing shown in FIG. 4, first, the system control apparatus 3 detects whether or not the endoscope 2 is connected (step S1).

If connection of the endoscope 2 is not detected in this case, the system control apparatus 3 stands by until the endoscope 2 is connected. Upon connection of the endoscope 2 being detected in this manner, the control portion 35 causes the monitor 6 to display a monitor screen 6a for selecting a medical treatment field as shown in FIG. 2, and allows a medical treatment field to be selected by an input operation from the input operation portion 34 (step S2).

Figure 2:
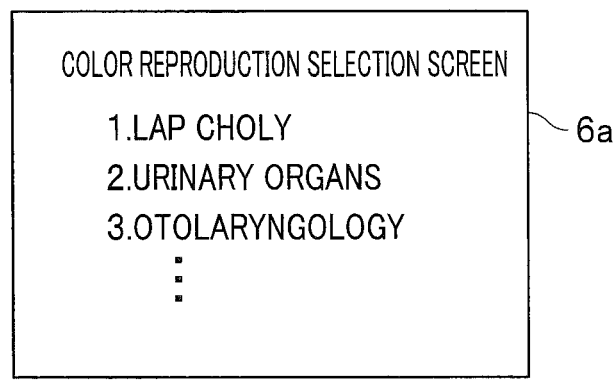
FIG. 2 is a view illustrating a display example of a monitor screen for selecting a medical treatment field in which the endoscope system is used in the aforementioned Embodiment 1.

FIG. 2 is a view that illustrates a display example of the monitor screen 6a for selecting a medical treatment field in which the endoscope system 1 is used. As described above, lap choly, urinary organs, otolaryngology and the like are displayed as selectable medical treatment fields on the monitor screen 6a.

Next, the control portion 35 determines whether or not the medical treatment field selected in step S2 is a predetermined field in which the laser probe 5 is used (step S3).

If the selected medical treatment field is a predetermined field, the control portion 35 controls the laser apparatus 4 so as to prohibit output of a laser beam from the irradiation portion 51 (step S4).

Next, the image processing portion 32 acquires an image of a single frame from the image pickup portion 25 (step S5), and the acquired image of a single frame is analyzed by the image analysis portion 33 (step S6) (image analysis step).

The analysis of the image by the image analysis portion 33 is performed as shown in the acquired image row and probe detection result row in the chart shown in FIG. 3. FIG. 3 is a chart that illustrates an example of setting permission or prohibition with respect to laser output based on a plurality of images that are time-sequentially acquired.

That is, the image analysis portion 33 analyzes a frame image and measures a number of pixels (and by extension, an area of the image portion 5i that is estimated to be the laser probe 5) that is included in a hue range that can be estimated as being a hue of the laser probe 5.

In a case where the number of pixels included in the hue range that can be estimated as being the hue of the laser probe 5 is equal to or greater than a predetermined number, the image analysis portion 33 determines that the laser probe 5 is detected in the frame image. The reason that a number of pixels that is equal to or greater than a predetermined number is used to determine that the laser probe 5 is detected is to avoid erroneous detection, and is also because it can be considered that a number of pixels that is equal to or greater than a predetermined number is detected in a case where the laser probe 5 protrudes by a required amount from the distal end opening of the channel 26.

More specifically, in the example illustrated in FIG. 3, until the time of a frame n that is acquired in a time-sequential manner, pixels included in a hue range that can be estimated as being the hue of the laser probe 5 are not detected. When a frame (n+1) is reached, although pixels included in the hue range are detected, it is determined that the laser probe 5 is not detected in the frame image since the predetermined number is not satisfied. Subsequently, from a frame (n+2) onwards, the number of pixels included in the hue range is equal to or greater than the predetermined number, and it is determined that the laser probe 5 is detected in the frame image.

Next, the control portion 35 converts the probe detection result obtained by the image analysis portion 33 into a logical value, and performs a logical operation (step S7) (control step).

More specifically, as shown in a logical value row in the chart in FIG. 3, the control portion 35 assigns a logical value "false" to frames in which the laser probe 5 is not detected and assigns a logical value "true" to frames in which the laser probe 5 is detected. Further, as shown in a logical product value row in the chart in FIG. 3, the control portion 35 calculates a logical product with respect to the logical values of, for example, two frames (however, the number of frames is not limited to two, and may be three or more) that are time-sequentially consecutive, that is, the logical value of the most recent frame and the logical value of a frame that immediately precedes the most recent frame.

In the example shown in FIG. 3, since the logical values up to the frame (n+1) are "false", the corresponding logical products are also "false". Although the logical value for the subsequent frame (n+2) is "true", because the logical value for the frame (n+1) that immediately precedes the frame (n+2) is "false", the logical product for the frame (n+2) is "false". Next, with respect to the subsequent frame (n+3), because the respective logical values for each of the frame (n+3) and the frame (n+2) are "true", the logical product for the frame (n+3) is "true". Similarly, the logical product for the frame (n+4) is "true".

Next, the control portion 35 determines whether or not the laser probe 5 protrudes from the distal end opening of the channel 26 based on whether or not the logical product is "true" (step S8) (control step). Thus, the control portion 35 is configured to determine that the laser probe 5 protrudes from the distal end opening only in a case where a plurality of (in this case, two) frames that are time-sequentially consecutive are "true".

In a case where it is determined in this manner in step S8 that the laser probe 5 protrudes from the distal end opening, the control portion 35 permits the laser apparatus 4 to output a laser beam from the laser probe 5 (step S9) (control step).

In contrast, if it is determined in step S8 that the laser probe 5 is not protruding from the distal end opening, the control portion 35 prohibits the laser apparatus 4 from outputting a laser beam from the laser probe 5 (step S10) (control step).

After the processing in step S9 or step S10 ends, the control portion 35 determines whether or not there is a next frame image (step S11).

If the control portion 35 determines in this case that there is a next frame image, the control portion 35 returns to step S5 and repeats the above described processing.

In contrast, if it is determined in step S11 that there is no next frame image, or if it is determined in step S3 that the selected medical treatment field is not a predetermined field that uses the laser probe 5, the present processing returns to the main control processing routine.

Thus, in a case where fields in which the endoscope system 1 is to be used are selectably displayed on the monitor 6, and a field that is selected through the input operation portion 34 is not a field in which the laser probe 5 is used, the control portion 35 is configured to skip the processing by the image analysis portion 33 and the control performed by the control portion 35 regarding whether or not to permit the output of a laser beam to thereby avoid the execution of unnecessary processing.

According to Embodiment 1 that is configured as described above, since whether or not the laser probe 5 is protruding from the distal end opening of the channel 26 is detected, and laser output is permitted only in a case where protrusion of the laser probe 5 is detected in accordance with a predetermined condition, laser output is not performed inside the channel 26 and thus damage to the endoscope 2 can be prevented and the safety thereof can be enhanced.

Because detection of a protruding state of the laser probe 5 from the distal end opening of the channel 26 is performed by image analysis, a dedicated sensor or the like is not required, and hence the weight and cost of the endoscope can be reduced. Further, a situation can be avoided in which a sensor malfunctions and detection of a protruding state of the laser probe 5 is not possible or the like. Further, it is possible to not only detect whether or not the laser probe 5 is protruding, but also to easily confirm the amount by which the laser probe 5 protrudes from the distal end opening of the channel 26.

At such time, since a configuration is adopted so as to permit laser output only when the laser probe 5 has been detected in a plurality of images that are time-sequentially consecutive, it is possible to stably detect the protruding state of the laser probe 5.

Further, since a configuration is adopted so that image analysis and control regarding whether to permit or not permit laser output is omitted in a case where field selection is performed and the selection result is that the field is not one in which the laser probe 5 is used, it is possible to decrease the load on the overall system.

In this way, the laser probe 5 can be stably and accurately detected in images, and the laser probe 5 can be used more safely.

[Embodiment 2]

Figure 6:
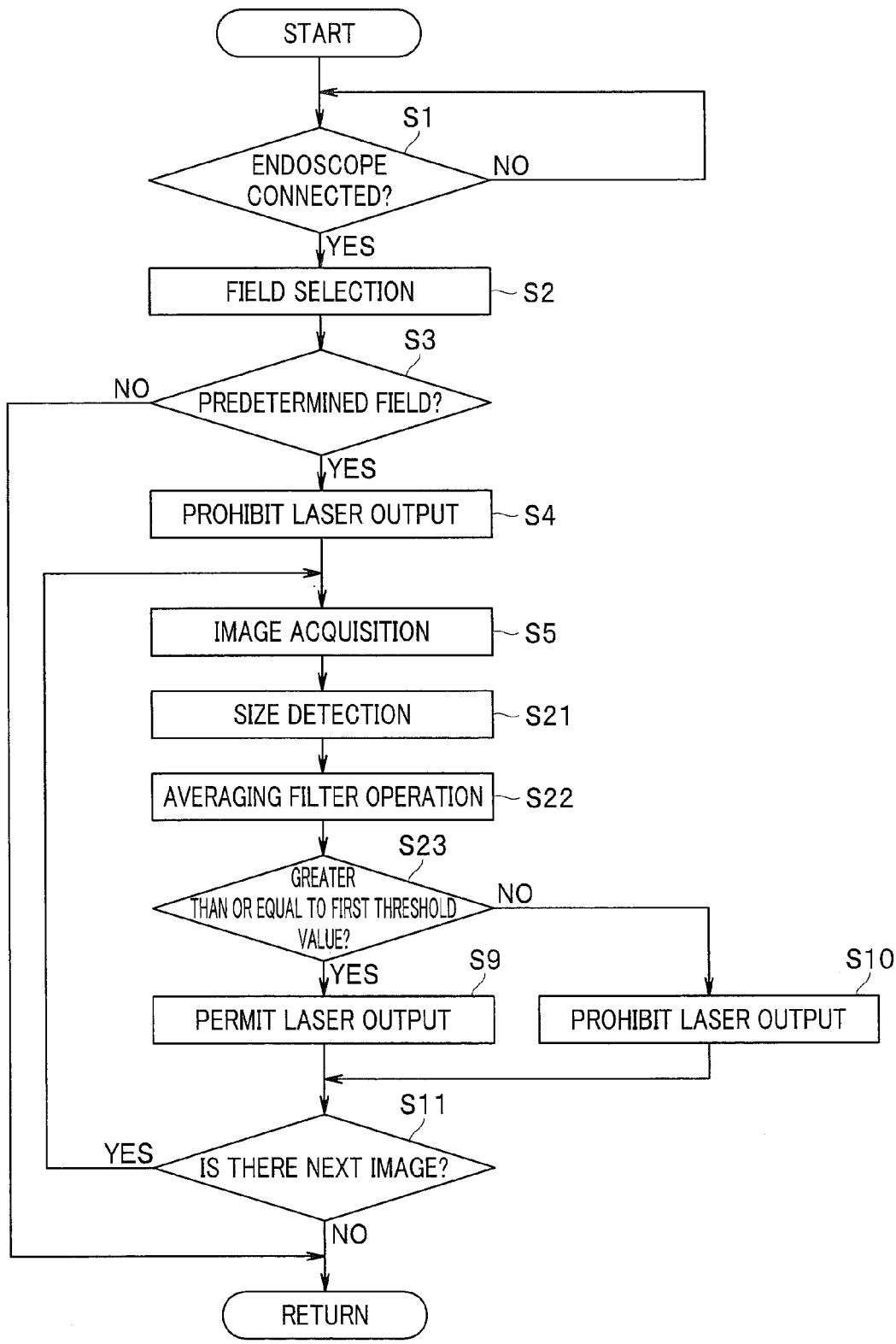
FIG. 6 is a flowchart illustrating operations of the endoscope system according to the aforementioned Embodiment 2.

FIG. 5 and FIG. 6 illustrate Embodiment 2 of the present invention. FIG. 5 is a chart illustrating an example in which permission/prohibition of laser output is set based on a plurality of images that are time-sequentially acquired. FIG. 6 is a flowchart illustrating operations of the endoscope system.

In Embodiment 2, portions that are the same as in the foregoing Embodiment 1 are denoted by the same reference numerals and a description thereof is omitted as appropriate, and mainly only differences relative to the foregoing Embodiment 1 are described.

In the foregoing Embodiment 1, permission/prohibition of laser output is controlled based on the result of a logical operation relating to whether or not the laser probe 5 is detected in a plurality of images that are time-sequentially consecutive. In the present embodiment, permission/prohibition of laser output is controlled based on an average value of an area of the image portion 5i showing the laser probe 5 in a plurality of images that are time-sequentially consecutive.

The configuration of the endoscope system 1 of the present embodiment is the same as the configuration shown in FIG. 1 of the foregoing Embodiment 1.

The operations of the endoscope system 1 (and by extension, a control method for the endoscope system) of the present embodiment will now be described in accordance with FIG. 6 while referring as appropriate to FIG. 5.

After the above-described processing from steps S1 to S5 is performed, the image analysis portion 33 performs image analysis on each of a plurality of images that are time-sequentially acquired, and detects the size of the image portion 5i showing the laser probe 5 in the respective images (step S21) (image analysis step).

The aforementioned detection of the size of the laser probe 5 by the image analysis portion 33 is performed as shown in an acquired image row and a probe size row in the chart in FIG. 5.

That is, the image analysis portion 33 analyzes a frame image and measures the number of pixels included in a hue range that can be estimated as being the hue of the laser probe 5. Although the number of pixels may also be used as the area of the image portion 5i that is estimated as being the laser probe 5, in this case conversion is performed from the number of pixels to an area of an arbitrary unit.

More specifically, in the example shown in FIG. 5, in the frames up to a frame n that are acquired time-sequentially, the size (area) of the laser probe 5 is 0. Thereafter, in a frame (n+1) the detected size of the laser probe 5 is 1, in a frame (n+2) the detected size is 2, in a frame (n+3) the detected size is 3, and in a frame (n+4) the detected size is 4.

Next, as shown in the average value row in the chart in FIG. 5, the control portion 35 calculates average values by performing an averaging filter operation with respect to the size of the image portion showing the laser probe 5 in the plurality of images that are time-sequentially consecutive (step S22) (control step). In this case the control portion 35 performs an averaging filter operation for the respective detected sizes of the laser probe 5 with respect to, for example, three frames (however, the number of frames is not limited to three, and it is sufficient that there is a plurality of frames) that are time-sequentially consecutive, that is, the most recent frame, the frame immediately preceding the most recent frame, and the frame that is two frames prior to the most recent frame.

In the example shown in FIG. 5, because the sizes detected up to and including the frame n are 0, the average values calculated by the averaging filter operation is 0. For the subsequent frame (n+1), a value (0+0+1)/3≈0.3 is the average value. Similarly, the average value for the frame (n+2) is 1, the average value for the frame (n+3) is 2, and the average value for the frame (n+4) is 3.

Next, the control portion 35 determines whether or not the laser probe 5 protrudes from the distal end opening of the channel 26 based on whether or not the average value calculated in step S22 is equal to or greater than a first threshold value (step S23) (control step). In this case, the reason that it is determined whether or not the average value is equal to or greater than the first threshold value is to avoid erroneous detection, and is also because it can be considered that the average value will be equal to or greater than the first threshold value in a case where the laser probe 5 protrudes by a required amount from the distal end opening of the channel 26.

In the example illustrated in FIG. 5, the first threshold value is set to 2. Accordingly, for the frames up to and including the frame (n+2) it is determined that the laser probe 5 is not protruding from the distal end opening of the channel 26, and for the frames (n+3), (n+4) . . . it is determined that the laser probe 5 protrudes from the distal end opening of the channel 26.

Thereafter, in step S9 and step S10, similarly to steps S9 and S10 of the foregoing Embodiment 1, output of a laser beam is permitted only in a case where it is determined in step S23 that the laser probe 5 is protruding from the distal end opening, and output of a laser beam is prohibited if it is determined that the laser probe 5 is not protruding from the distal end opening.

According to Embodiment 2, in addition to obtaining substantially the same advantageous effects as in the above described Embodiment 1, since protrusion of the laser probe 5 from the distal end opening is determined based on an average value of the size of the image portion 5i showing the laser probe 5 in images of a plurality of frames that are time-sequentially consecutive, even if an inappropriate detection result is obtained for a specific frame, it is possible to avoid an erroneous detection overall.

Further, by setting the first threshold value to a desired value, it is possible to adjust the extent to which the laser probe 5 should protrude from the distal end opening before laser output is permitted.

[Embodiment 3]

Figure 8:
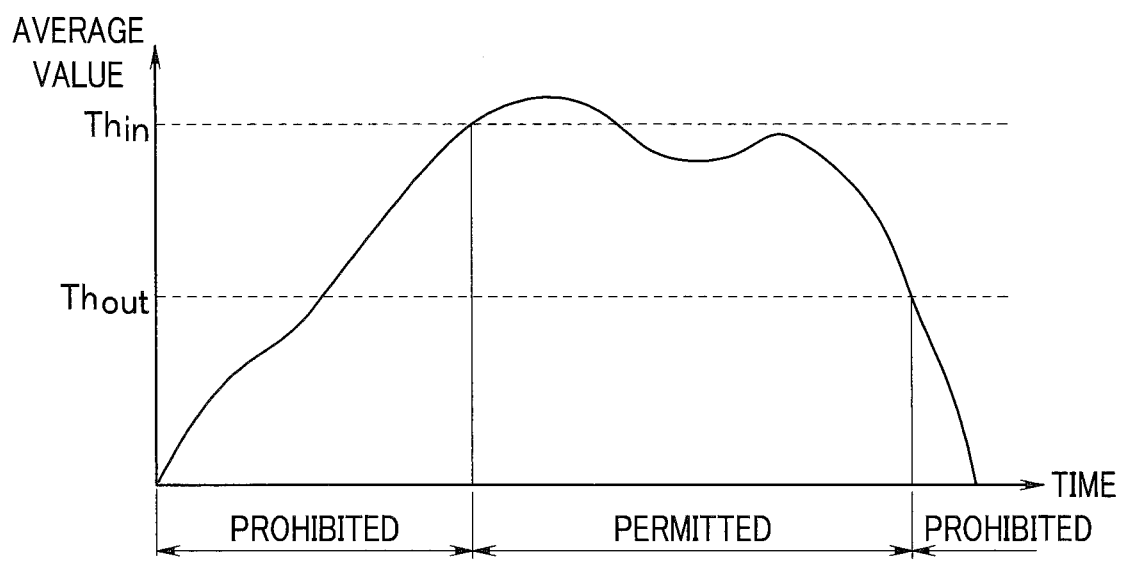
FIG. 8 is a diagram illustrating an example in which threshold values are made to differ between a time of changing from prohibiting to permitting laser output and a time of changing from permitting to prohibiting laser output in the aforementioned Embodiment 3.

FIG. 7 to FIG. 9 illustrate Embodiment 3 of the present invention. FIG. 7 is a chart illustrating an example in which permission/prohibition of laser output is set based on a plurality of images that are time-sequentially acquired. FIG. 8 is a diagram illustrating an example in which threshold values are made to differ between a time of changing from prohibiting to permitting laser output and a time of changing from permitting to prohibiting laser output. FIG. 9 is a flowchart illustrating operations of the endoscope system.

In Embodiment 3, portions that are the same as in the foregoing Embodiments 1 and 2 are denoted by the same reference numerals and a description thereof is omitted as appropriate, and mainly only differences relative to the foregoing Embodiments 1 and 2 are described.

Relative to the above described Embodiment 2, in the present embodiment a threshold value (second threshold value) for a time of changing from permitting laser output to prohibiting laser output is additionally provided that is different from the first threshold value for changing from prohibiting to permitting laser output.

The configuration of the endoscope system 1 of the present embodiment is the same as the configuration shown in FIG. 1 of the above described Embodiment 1.

The operations of the endoscope system 1 (and by extension, a control method for the endoscope system) of the present embodiment will now be described in accordance with FIG. 9 while referring as appropriate to FIG. 7 and FIG. 8.

After performing the processing in the above described steps S1 to S3, if it is determined in step S3 that the selected medical treatment field is a predetermined field, the control portion 35 controls the laser apparatus 4 so as to prohibit the output of a laser beam from the irradiation portion 51, and also sets a permission flag that indicates a permission/prohibition state with respect to output of a laser beam to "off" (step S4A).

The processing in steps S5, S21 and S22 is then performed as described above.

Next, the control portion 35 determines whether or not the permission flag is set to "on" (step S31) (control step).

In this case, if the permission flag is set to "off", it means that laser output is currently being prohibited, and thus control is performed regarding whether or not to change from prohibiting to permitting laser output. Therefore, the processing in step S23 is performed as described above, and if the average value is equal to or greater than the first threshold value, the control portion 35 permits the laser apparatus 4 to output a laser beam from the laser probe 5 and also sets the permission flag with respect to the laser output to "on" (step S9A) (control step).

Further, in step S31, if the permission flag is set to "on", it means that laser output is currently being permitted, and thus control is performed regarding whether or not to change from permitting to prohibiting laser output.

At this time, the control portion 35 determines whether or not the laser probe 5 is no longer protruding from the distal end opening of the channel 26 based on whether or not the average value is less than the second threshold value (step S32) (control step). In this case, the second threshold value is set so as to be a smaller value than the first threshold value, for example, it is assumed that the first threshold value is set to 2 and the second threshold value is set to 1.

The situation at a time that the laser probe 5 returns into the channel 26 will now be described referring to FIG. 7.

In the example illustrated in FIG. 7, the size (area) of the laser probe 5 is 4 in the frames that are time-sequentially acquired up to and including frame n. Thereafter, it is assumed that the detected size (area) is 3 in the frame (n+1), the detected size (area) is 2 in the frame (n+2), the detected size (area) is 1 in the frame (n+3), and the detected size (area) is 0 from the frame (n+4) onwards.

At this time, the average values that are calculated by the averaging filter operations are 4 for the frames up to and including the frame n, (4+4+3)/3≈3.7 for the frame (n+1), (4+3+2)/3=3 for the frame (n+2), (3+2+1)/3=2 for the frame (n+3), (2+1+0)/3=1 for the frame (n+4), and (1+0+0)/3≈0.3 for the frame (n+5) and the like.

Accordingly, in step S32, because the average value up to and including the frame (n+4) is 1 or more, laser output continues to be permitted.

On the other hand, in step S32, if it is determined that the average value is less than the second threshold value, the control portion 35 prohibits the laser apparatus 4 from outputting a laser beam from the laser probe 5 and also sets the permission flag with respect to laser output to "off" (step S10A) (control step).

That is, in the example illustrated in FIG. 7, because the average value becomes 0.3 when the frame (n+5) is reached, that is, the average value becomes less than 1 that is the second threshold value, it is determined that the laser probe 5 no longer protrudes from the distal end opening of the channel 26, and thus the processing in step S10A is performed. That is, after permitting output of a laser beam, the control portion 35 prohibits the output of a laser beam from the laser probe 5 only in a case where the average value is less than the second threshold value that is less than the first threshold value.

Thus, in a case where the processing in step S9A or step S10A is performed, or it is determined that the average value is less than the first threshold value in step S23, or it is determined in step S32 that the average value is equal to or greater than the second threshold value, the control portion 35 proceeds to the processing in step S11 that is described above.

When processing is performed is this manner, for example, as shown in FIG. 8, the state regarding permission/prohibition of the laser output changes.

That is, at a time that laser output is being prohibited, the laser output will not be permitted until the average value calculated in step S22 becomes a first threshold value $Th_{in}$. Upon the average value becoming equal to or greater than the first threshold value $Th_{in}$, the laser output is permitted. Thereafter, even if the average value becomes less than the first threshold value $Th_{in}$, the control does not transition from permission to prohibition of laser output as long as the average value is equal to or greater than a second threshold value $Th_{out}$. Subsequently, the laser output is prohibited upon the average value becoming less than the second threshold value $Th_{out}$.

Thus, according to Embodiment 3, in addition to obtaining substantially the same advantageous effects as in the above described Embodiment 2, once the average value becomes equal to or greater than the first threshold value $Th_{in}$ and laser output is permitted, laser output is not prohibited as long as the average value does not become less than the second threshold value $Th_{out}$ that is less than the first threshold value $Th_{in}$. Accordingly, even if the average value rises and falls in a range of narrow values that sandwiches the first threshold value $Th_{in}$, the state regarding permission and prohibition of the laser output does not change minutely. Thus, it is possible to stably utilize laser output once the laser output has been permitted, and the operability can be improved.

Note that although an endoscope system has been mainly described in the foregoing description, the present invention may be a control method that controls an endoscope system as described above, or a control program for causing a computer to control an endoscope system as described above, or a non-transitory computer-readable recording medium that records the control program or the like.

Further, the present invention is not limited to the precise embodiments described above, and can be embodied in the implementing stage by modifying the components without departing from the scope of the invention. Also, various aspects of the invention can be formed by appropriately combining a plurality of the components disclosed in the embodiments described above. For example, some components may be deleted from all of the disclosed components according to the embodiments. Furthermore, components from different embodiments may be appropriately combined. Thus, naturally various modifications and applications are possible within a range that does not deviate from the spirit and scope of the present invention.

What is claimed is:

1. An endoscope system, comprising:
an endoscope having an insertion portion that is to be inserted into a subject, an objective optical system provided in a distal end portion of the insertion portion, an image pickup portion that time-sequentially picks up optical images of the subject that are formed by the objective optical system to acquire a plurality of images, and a channel that is provided inside the insertion portion so as to have a channel opening in the distal end portion of the insertion portion;
a laser probe that is inserted through the channel of the endoscope and that outputs a laser beam from a distal end portion towards the subject;
an image analysis portion that detects an area of the laser probe with respect to each of a plurality of the images that are time-sequentially acquired; and
a control portion that determines whether or not the laser probe protrudes from the channel opening based on detection results with respect to the area of the laser probe which are obtained by the image analysis portion for a plurality of the images that are time-sequentially consecutive, and permits the laser probe to output the laser beam only in a case where it is determined that the laser probe protrudes.

2. The endoscope system according to claim 1, wherein:
with respect to each of a plurality of the images that are time-sequentially acquired by the image pickup portion, the image analysis portion detects an area of an image portion that is included in a hue range of the laser probe as the area of the laser probe.

3. The endoscope system according to claim 1, wherein:
the control portion performs a logical product operation that takes a case where an area of the laser probe that is equal to or greater than a predetermined area is detected as "true" and a case where an area of the laser probe that is equal to or greater than the predetermined area is not detected as "false" for a plurality of the images that are time-sequentially consecutive, and permits the laser probe to output the laser beam only in a case where an operation result is "true".

4. The endoscope system according to claim 1, wherein:
the control portion calculates an average value by performing an averaging filter operation with respect to an area of the laser probe in a plurality of the images that are time-sequentially consecutive, and permits the laser probe to output the laser beam only in a case where the average value is equal to or greater than a first threshold value.

5. The endoscope system according to claim 4, wherein:
after permitting output of the laser beam, the control portion prohibits the laser probe from outputting the laser beam only in a case where the average value becomes less than a second threshold value that is smaller than the first threshold value.

6. The endoscope system according to claim 1, further comprising:
a display apparatus that displays the image; and
an input operation portion for performing an operation input,
wherein the control portion causes the display apparatus to selectably display fields in which the endoscope system is to be used, the control portion controls processing by the image analysis portion to be skipped and controls by the control portion for determining whether or not to permit output of the laser beam be skipped in response to a field being selected through the input operation portion that is not a predetermined field in which the laser probe is to be used, and the control portion controls the processing by the image analysis portion to be performed and the controls by the control portion for determining weather or not to permit the output of the laser beam to be performed in response to the field being selected through the input operation portion being the predetermined field in which the laser probe is to be used.

7. The endoscope system according to claim 1, wherein:
the image pickup portion acquires a plurality of frame images, and
the image analysis portion detects an area of an image portion occupied by the laser probe in one frame image acquired by the image pickup portion, and analyzes each of the plurality of frame images that are time-sequentially acquired.

8. An operation method of an endoscope system which includes: an endoscope having an insertion portion that is to be inserted into a subject, an objective optical system provided in a distal end portion of the insertion portion, an image pickup portion that time-sequentially picks up optical images of the subject that are formed by the objective optical system to acquire a plurality of images, and a channel that is provided inside the insertion portion so as to have a channel opening in the distal end portion of the insertion portion, and a laser probe that is inserted through the channel of the endoscope and that outputs a laser beam from a distal end portion towards the subject:

the operation method comprising:
a step of detecting, by an image analysis portion, an area of the laser probe with respect to each of a plurality of the images that are time-sequentially acquired; and
a step of determining, by a control portion, whether or not the laser probe protrudes from the channel opening based on detection results with respect to the area of the laser probe which are obtained in the detecting step for a plurality of the images that are time-sequentially consecutive, and permitting the laser probe to output the laser beam only in a case where it is determined that the laser probe protrudes.

* * * * *

UNITED STATES PATENT AND TRADEMARK OFFICE
CERTIFICATE OF CORRECTION

| | |
|---|---|
| PATENT NO. | : 9,579,011 B2 |
| APPLICATION NO. | : 14/733303 |
| DATED | : February 28, 2017 |
| INVENTOR(S) | : Kotaro Ogasawara et al. |

It is certified that error appears in the above-identified patent and that said Letters Patent is hereby corrected as shown below:

In the Claims

Column 12, Line 60 (Claim 6) should read: whether or not to permit output of the laser beam to be Signed and Sealed this
Twenty-third Day of May, 2017

Michelle K. Lee
*Director of the United States Patent and Trademark Office*